United States Patent
Fabricius

(10) Patent No.: US 11,559,544 B2
(45) Date of Patent: *Jan. 24, 2023

(54) COMBINATION OF A MAPK/ERK PATHWAY INHIBITOR AND A GLYCOSAMINOGLYCAN FOR THE TREATMENT OF CANCER

(71) Applicant: CELL RECEPTOR AG, Geneva (CH)

(72) Inventor: Hans-Ake Fabricius, Esgrus (DE)

(73) Assignee: Cell Receptor AG, Geneva (CH)

(*) Notice: Subject to any disclaimer, the term of this patent is extended or adjusted under 35 U.S.C. 154(b) by 6 days.

This patent is subject to a terminal disclaimer.

(21) Appl. No.: 16/640,106

(22) PCT Filed: Aug. 23, 2018

(86) PCT No.: PCT/EP2018/072749
§ 371 (c)(1),
(2) Date: Feb. 19, 2020

(87) PCT Pub. No.: WO2019/038367
PCT Pub. Date: Feb. 28, 2019

(65) Prior Publication Data
US 2021/0128603 A1    May 6, 2021

(30) Foreign Application Priority Data
Aug. 23, 2017 (EP) .................... 17187413

(51) Int. Cl.
| | | |
|---|---|---|
| *A61K 31/737* | (2006.01) |
| *A61K 31/416* | (2006.01) |
| *A61K 31/437* | (2006.01) |
| *A61K 31/506* | (2006.01) |
| *A61P 35/00* | (2006.01) |
| *A61K 45/06* | (2006.01) |
| *A61K 35/04* | (2006.01) |

(52) U.S. Cl.
CPC .......... *A61K 31/737* (2013.01); *A61K 31/416* (2013.01); *A61K 31/437* (2013.01); *A61K 31/506* (2013.01); *A61K 35/04* (2013.01); *A61K 45/06* (2013.01); *A61P 35/00* (2018.01)

(58) Field of Classification Search
None
See application file for complete search history.

(56) References Cited

U.S. PATENT DOCUMENTS

2014/0134158 A1    5/2014    Bardelli

FOREIGN PATENT DOCUMENTS

| WO | 2015/059177 A1 | 4/2015 |
| WO | 2015/161230 A1 | 10/2015 |

OTHER PUBLICATIONS

Akinleye, Journal of Hematology & Oncology 2013, 6:27. (Year: 2013).*
O'Shea, Oncotarget, 2017, vol. 8, No. 29, pp. 85120-85135. (Year: 2017).*
Int'l. Search Report for PCT/EP2018/072749, dated Oct. 31, 2018.
Claire Louise Cold, et al., "Oligosaccharides as anti-angiogenic agents", Expert Opinion on Biological The, Informa Healthcare, Ashley, London; GB, vol. 8, No. 3, Jan. 1, 2008 (Jan. 1, 2008), pp. 351-362, XP009123682, ISSN: 1471-2598the whole document.
Dooley A.J., et al., "Intermittent dosing with vemurafenib in BRAF V600E—mutant melanoma: Review of a case series", Therapeutic Advances in Medical Oncologyenglandjan, Sage, UK, vol. 6, No. 6, Jan. 1, 2014 (Jan. 1, 2014), pp. 262-266, XP009183235, ISSN: 1758-8340, DOI: 10.1177/1758834014548187 the whole document.

* cited by examiner

*Primary Examiner* — Layla D Berry
(74) *Attorney, Agent, or Firm* — Blue Filament Law PLLC

(57) ABSTRACT

A negatively charged glycosaminoglycan is provided for use as a medicament for the treatment of cancer. A combined administration of a negatively charged glycosaminoglycan is provided in which the glycosaminoglycan is characterised by the absence of the terminal pentasaccharide of Heparin, and an inhibitor of the MAPK/ERK pathway. A combined administration of a glycosaminoglycan and a MAPK/ERK pathway inhibitor is provided as a medicament for the treatment of cancer types that exhibit a resistance towards a single MAPK/ERK pathway inhibitor treatment.

20 Claims, 2 Drawing Sheets

Figure 1:
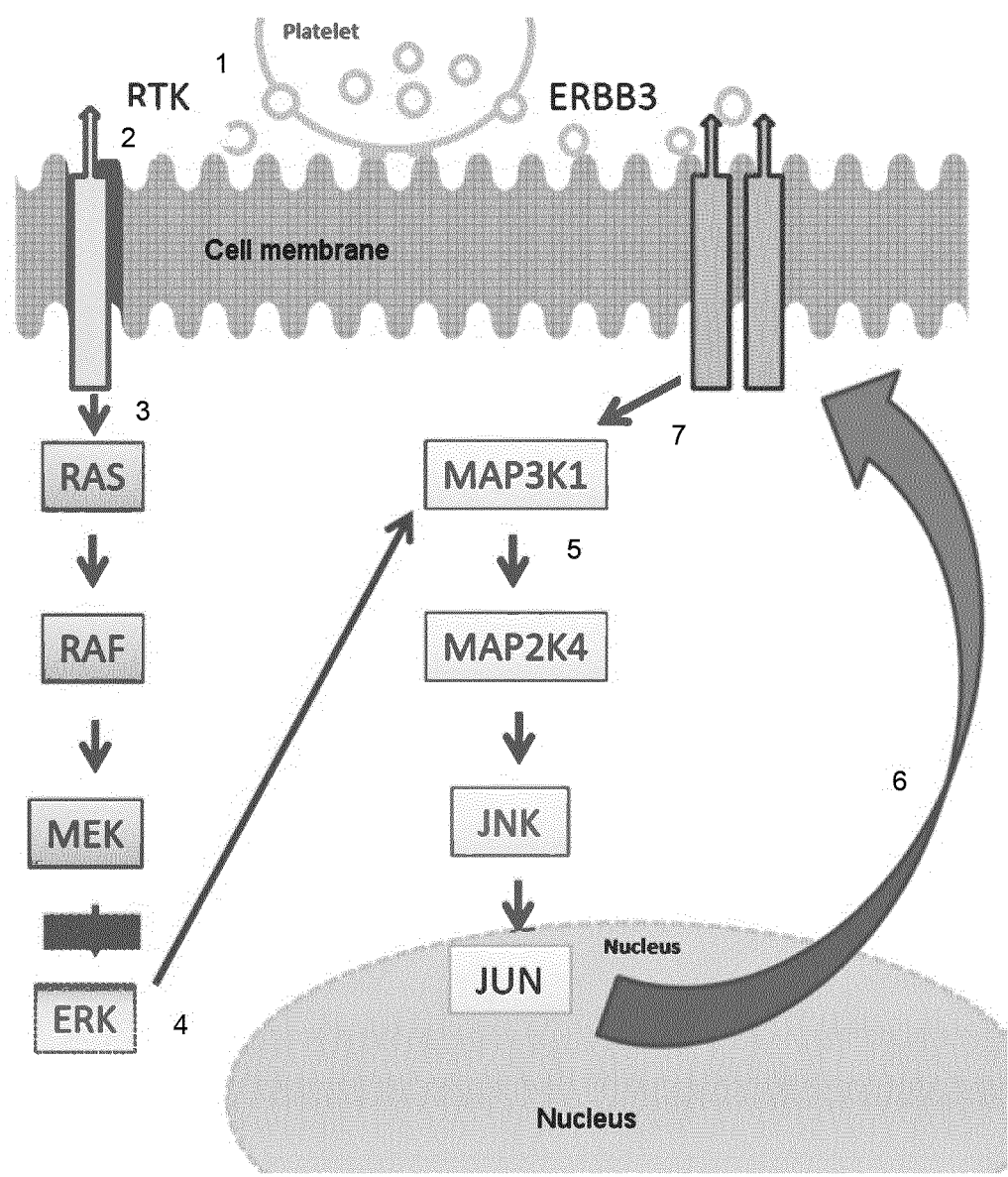

COMBINATION OF A MAPK/ERK PATHWAY INHIBITOR AND A GLYCOSAMINOGLYCAN FOR THE TREATMENT OF CANCER

The invention relates to a negatively charged glycosaminoglycan for use as a medicament for the treatment of cancer, comprising the combined administration of a negatively charged glycosaminoglycan, wherein said glycosaminoglycan is characterised by the absence of the terminal pentasaccharide of Heparin, and an inhibitor of the MAPK/ERK pathway. The invention also encompasses a combined administration of a glycosaminoglycan and a MAPK/ERK pathway inhibitor as a medicament for the treatment of cancer types that exhibit a resistance towards a single MAPK/ERK pathway inhibitor treatment.

BACKGROUND OF THE INVENTION

A goal of modern cancer therapy is to identify molecules in signal transduction pathways that affect cell growth, and particularly those that cause a normal cell to become cancerous. One such pathway is the MAPK/ERK pathway, also referred to as the Ras-Raf-MEK-ERK pathway or Raf-MEK-ERK, and the up-regulation of one or more of its members is thought to be responsible for a number of cancers.

Constitutive action of MAPKs has been reported in over 30% of primary tumour cell lines including cell lines derived from colon, lung, breast, pancreas, ovary, and kidney (Hoshino et al. 1999). Higher concentrations of active MAPK/ERK (pMAPK/pERK) have also been detected in tumour tissue as compared to normal adjacent tissue (Sivaraman et al. 1997.)

The MAPK/ERK pathway has been identified to mediate proliferative and anti-apoptotic signalling from growth factors and oncogenic factors such as Ras (e.g. KRAS, NRAS, and HRAS) and Raf (e.g. BRAF) mutant phenotypes that have been identified in numerous cancers and promote tumour growth, progression, and metastasis.

Due to its role in the mediation of growth-promoting signals from multiple growth factor receptors, compounds of the MAPK/ERK pathway are molecular targets with potentially broad therapeutic applications, particular with respect to the treatment of cancer, but also in the treatment of other disorders associated with unwanted cell proliferation.

The MAPK/ERK pathway is a membrane-to-nucleus signalling module that is highly conserved among metazoans. At the starting point of the pathway a ligand (e.g., a growth factor, cytokine, or hormone) binds to the extracellular portion of a receptor tyrosine kinase (RTK), which causes phosphorylation of their cytoplasmic domains. The activation of the RTK enables cytoplasmic adaptor proteins to recruit guanine-nucleotide exchange factors (GEFs), which activate the small GTPase RAS by catalyzing the exchange of GDP for GTP. Ras in turn activates Raf, which functions as a MAP kinase kinase kinase (MAPKKK or MAP3K). Subsequently Raf phosphorylates and activates MAP kinase kinases (MAPKK), which are referred as MEKs (MAPK or ERK kinases) in the pathway. MEK phosphorylates and activates the third and final enzyme in the pathway that is a MAP kinase (MAPK) referred to as ERK (extracellular signal-regulated kinase). Once activated, ERKs can translocate into the nucleus where they phosphorylate transcription factors, thereby regulating the activity in critical cell processes such growth factor-induced gene regulation, cell cycle entry or cell differentiation (Peyssonnaux et al. 2001).

In the MAPK/ERK pathway MEKs (in particular MEK1s and MEK2s) occupy a strategic downstream position in catalyzing the phosphorylation of its MAPK substrates, ERK1 and ERK2 (Anderson et al. 1990). Due to its high selectivity for the substrates ERK1 and ERK2 and its unique ability to act as a dual-specificity kinase, MEKs take a central role in the integration of signals into the MAPK pathway. Frequently MEKs are deregulated in human cancer as a result of activating mutations in the BRAF and RAS genes (KRAS, NRAS, and HRAS). Given the high prevalence of ERK signalling aberrations and the dependence of RAS and BRAF mutant tumours on these oncogenic drivers, intense efforts are under way to identify inhibitors of this pathway for use as anticancer therapies.

RAF inhibitors vemurafenib and dabrafenib, have shown remarkable clinical activity in patients with BRAF V600E or BRAF V600K melanomas (Flaherty et al. 2010. Chapman et al. 2011, Hauschild et al. 2012). Likewise, a number of highly specific and potent MEK1/2 inhibitors have been developed and evaluated in clinical studies. For instance, trametinib administration has been proven as a successful therapeutic strategy in treating patients with a BRAF-V600 mutation and non-resectable or metastasized melanoma (Lugowska et al. 2015). However, many MEK inhibitory agents also exhibited only limited efficacy in single-agent therapies in clinical trials (Y. Zhao et al 2015).

Moreover, as has been the pattern with inhibitors of other oncogenic kinases, the clinical benefit of therapies based upon inhibition of the target kinases Raf or MEK have been limited by the emergence of drug resistance (Poulikakos et al. 2011, Rosen et al. 2013).

Strategies by combined treatment using multiple agents have shown promising results. For instance, the combination of MEK inhibitors with Raf inhibitors improves therapeutic efficacy (WO 2009/018238A, Eroglu et al. 2016). Also a combined administration of MEK inhibitors with BTK inhibitors has been proposed (WO 2017/033113A1). US 2014/134158 A1, WO 2015/161230 A1 and Dooley A. et al. 2014 also propose the use of MAPK/MEK inhibitors in the treatment of cancer. However, even with combined therapeutic approaches, disease progression and development of resistance has been observed (Grimaldi et al. 2017).

A need for further pharmacological therapies for the treatment of cancers associated with aberrant MAPK/ERK pathway activity continues to exist.

Claire Louise Cole at al. propose the use of Oligosaccharides as inhibitors for angiogenesis (Cole et al 2010). Furthermore, recently an anti-proliferative treatment has been proposed that relies on impeding the physical interaction between platelets and the surface of proliferating cancerous cells (WO 2015/059177A1).

As shown in WO 2015/059177A1, sulfated glycosaminoglycans interfere with the physical interaction of platelets with the surface of cancerous cells, which may reduce or even halt proliferation and thus tumour growth.

The approach described therein is different but complementary to the observation that platelets bind to the surface of tumour cells, and that this binding is involved in tumour metastasis. For example, Modery-Pawlowski et al. 2013 and Takagi et al. 2013 disclosed that a physical interaction between platelets and tumour cells plays an important role in the metastasis of tumour cells.

The mechanism for the inhibition of proliferation of cancerous cells via disrupting the platelet-cell surface interaction likely relies on impeding growth factors, which are transported by platelets to the cancerous cells.

Growth factors are essential for the growth of normal and malignant cells, and must be made available to proliferating cells. Cells that have left the G0 phase and are poised in the G1 phase, require appropriate signals regarding entry into S phase and associated cell proliferation. To a large extent growth factors are however not available as free substances in the blood in vivo, but rather in vesicles within platelets, which thus provide the growth factors. Furthermore, due to the physical interaction of platelets with the surface of the tumour cells and the topology implied therein, the growth factors are released at the specific, necessary locations for cell proliferation.

Despite advances made with respect to developing inhibitors of the MAPK/ERK pathway, a significant need exists in the art for treating cancers cells resistant to such inhibitors, or for preventing or reducing the risk or frequency of the appearance of such resistance.

As described herein, the combined administration of inhibitors of the MAPK/ERK pathway together with negatively charged glycosaminoglycans represents a surprisingly effective therapeutic approach for treating various tumours, in particular with respect to treating tumours resistant to or at risk of becoming resistant to MAPK/ERK pathway inhibitors.

SUMMARY OF THE INVENTION

In light of the prior art the technical problem underlying the present invention is to provide alternative means for the treatment of cancer. A further objective of the present invention is the provision of means for treating tumours resistant to or at risk of becoming resistant to MAPK/ERK pathway inhibitors.

This problem is solved by the features of the independent claims. Preferred embodiments of the present invention are provided by the dependent claims.

The invention therefore relates to a negatively charged glycosaminoglycan for use as a medicament for the treatment of cancer, comprising the combined administration of
(1) a negatively charged glycosaminoglycan, wherein said glycosaminoglycan is characterised by the absence of the terminal pentasaccharide of Heparin, and
(2) an inhibitor of the MAPK/ERK pathway.

The inhibitors of the MAPK/ERK pathway may relate to any molecule that targets an interaction with one of the compounds of the MAPK/ERK pathway cascade and thus leads to a reduction of the MAPK/ERK pathway activity. The inhibitors induce in particular an inhibitory function on one or more of the enzymes of the MAPK/ERK cascade including the receptor tyrosine kinase (RTK), the small GTPase Ras, Raf, MEK or ERK. As described above, aberrant MAPK/ERK signalling activity is involved in numerous cancerous diseases, leading to a number of promising therapeutic approaches based upon inhibitors of the pathway.

However, for many identified potent inhibitors of enzymes of the MAPK/ERK signalling cascade, escape mechanisms have been observed, which lead to resistance and low therapeutic efficacy in clinical trials.

It is a surprising finding of the inventor that such "escape events" from MAPK/ERK inhibitory treatments (i.e. the escape of a tumour via development or strengthening of MAPK/ERK inhibitor resistance) can however be overcome, when combining the administration of a MAPK/ERK inhibitor with a negatively charged glycosaminoglycan.

Glycosaminoglycans (GAGs) are large preferably linear polysaccharides constructed of repeating disaccharide units. Primary configurations preferably comprise an amino sugar (either GlcNAc or GalNAc) and an uronic acid (either glucuronic acid and/or iduronic acid).

Previously, it has been shown that sulfated glycosaminoglycan may compromise the physical interaction between platelets (i.e. thrombocytes) and cancerous cells. More generally, it is the negative charge of glycosaminoglycans that is the determining feature of the mechanism underlying the inhibition of the platelet-cell binding described above.

Virtually all mammalian cells produce proteoglycans and secrete them into the ECM, insert them into the plasma membrane, or store them in secretory granules. Cell membranes, in particular of cells committed to proliferation, therefore possess structures resembling negatively charged glycosaminoglycans, which are able to bind platelets. Negatively charged glycosaminoglycans of the present invention may act competitively, in that they block a membrane receptor molecule, e.g. on the platelets, which would otherwise be responsible for recognizing the negatively charged surface molecules on the membrane of the cancerous cells. It is thus the negative charge of the glycosaminoglycans that provide the compounds with their inhibitory function on the platelet-cancer cell interaction.

Particularly preferred negatively charged glycosaminoglycans relate to sulfated glycosaminoglycans, however also non-sulfated glycosaminoglycans that possess a negative charge may be used according to the disclosed invention.

In some embodiments, other negatively charged glycosaminoglycans relate to glycosaminoglycans comprising one or more butanoate anions, or butyrated glycosaminoglycans, i.e. glycosaminoglycans functionalized with butyrate to exhibit a corresponding negative charge. Such molecules may be termed butanoylated glycosaminoglycans, such as butanoylated LMWH.

For example, hyaluronic acids may also be employed. By disturbing the signalling activity of platelets on cancerous cells, negatively charged glycosaminoglycans exhibit an inhibitory function on the cells. As used herein the term negatively charged glycosaminoglycan does not qualify however as an inhibitor of the MAPK/ERK pathway, since the glycosaminoglycan do not directly interfere with enzymes of the MAPK/ERK pathway, but with the physical interaction of platelets with the cancerous cells, only downstream effecting cellular signalling, by impeding the provision of growth factors.

As discovered by the inventor, the combined administration of an inhibitor of the MAPK/ERK pathway together with negatively charged glycosaminoglycan provides a synergistic therapeutic effect in the treatment of cancerous diseases, greater than the sum of each individual effect, when considered in an isolated fashion.

Based upon the insight gained from previous studies, it is assumed that treatment failure and/or resistance to inhibitors of the MAPK/ERK pathway can be largely attributed to growth factor dependent escape routes.

For instance, inhibition of the MAPK/ERK pathway by interfering with the function MEK, e.g. by MEK inhibitor selumetinib, may result in the activation of an alternative signalling pathway via non-phosphorylated ERK inducing the production of further RTK proteins, such as Erb-family proteins. Thereby a signalling chain parallel to Ras signalling is activated, which e.g. in the case of Erbb3 may promote cell growth through a membrane-nucleus signalling module via MAP3K1 and MAP2K4 (see FIG. 1). Even though the MEK inhibitor may efficiently disrupt phosphorylation of Erk and thus Ras signalling in the cancerous cells, the parallel Erb-family protein dependent pathway allows for a continuous support of proliferation and tumour growth.

Similarly, studies have suggested that a resistance to the BRAF inhibitor vemurafenib can be attributed to increased signalling through the epidermal growth factor receptor (EGFR) of the Erb protein family. While at baseline levels the BRAF→MEK→ERK signalling activates a negative feedback loop that serves to attenuate the RTK EGFR signalling, BRAF inhibition by vemurafenib relieves the negative feedback, leading to increased signalling through the EGFR. Thereby inducing a positive membrane-to-nucleus signalling via PI3K in support of proliferation. The on-target activity of a single therapeutic BRAF inhibitor may thus in certain cancers, in particular metastatic colorectal and thyroid cancers, activate a rapid, adaptive mechanism of chemoresistance (Holderfield et al. 2014).

Surprisingly however, the combined administration of negatively charged glycosaminoglycans may effectively interfere with such signalling escape routes for inhibitors of the MAPK/ERK pathway. Without wishing being to be bound by theory, the inventor is convinced that the escape routes to the MAPK/ERK pathway inhibitors rely on a growth factor dependent activation of proteins of the Erb family, which are increasingly produced in response a partial or entire inhibition of the MAPK/ERK pathway. The administration of negatively charged glycosaminoglycans likely interferes with the escape route by diminishing the supply of growth factors, necessary for the activation of the Erb-protein dependent alternative signalling route, via prohibiting platelet delivered growth factors.

As described above, negatively charged glycosaminoglycans exhibit strong inhibitory function on the platelet-cell-surface interaction, in particular, regarding cancerous cells. Considering that platelets represent a major source of growth factors in vivo, the interference with the platelets, and thus with the provision of growth factors, is a likely explanation for the synergistic effect of the combined administration of negatively charged glycosaminoglycans and inhibitors of the MAPK/ERK pathway in the treatment of cancer.

The combined administration of the present invention is expected to be particularly useful for the treatment of patients with cancers, including, but not limited to, non-solid tumours such as leukaemia, for example acute myeloid leukaemia, multiple myeloma, haematologic malignancies or lymphoma, and also solid tumours and their metastases such as melanoma, non-small cell lung cancer, glioma, hepatocellular (liver) carcinoma, glioblastoma, carcinoma of the thyroid, bile duct, bone, gastric, brain/CNS, head and neck, hepatic, stomach, prostate, breast, renal, testicular, ovarian, skin, cervical, lung, muscle, neuronal, oesophageal, bladder, lung, uterine, vulval, endometrial, kidney, colorectal, pancreatic, pleural/peritoneal membranes, salivary gland, and epidermoid tumours and haematological malignancies.

The combined administration of the invention is expected to be especially useful for the treatment of patients with lung cancer, melanoma, gastric cancer, colorectal cancer, ovarian cancer, thyroid cancer, pancreatic cancer, liver cancer, and their metastases, and also for the treatment of patients with acute myeloid leukaemia or multiple myeloma.

The combined administration of the present invention is also expected to be particularly useful for the treatment of patients with a tumour which is associated with the MAPK/ERK (Ras-Raf-MEK-ERK) pathway or which is dependent alone, or in part, on the biological activity of the MAPK/ERK (Ras-Raf-MEK-ERK) pathway. Cancers associated with the biological activity of the MAPK/ERK (Ras-Raf-MEK-ERK) pathway may be determined by a skilled person using common molecular biological techniques for assessing expression or protein amounts of any one of the members of this pathway.

The combination of treatments of the present invention is also expected to be particularly useful for the treatment of patients with a tumour which is associated with MEK or which is dependent alone, or in part, on the biological activity of MEK.

The combination of treatments of the present invention is also expected to be particularly useful for the treatment of patients with a tumour which is associated with Raf or which is dependent alone, or in part, on the biological activity of Raf.

Moreover, according to some embodiments of the invention, it is preferred to administer negatively charged glycosaminoglycans that are characterised by the absence of the terminal pentasaccharide of Heparin. The sulfated glycosaminoglycan Heparin is well known for its anticoagulation activity, which it mainly achieves by an inhibition of the clotting factor Xa and thrombin. The primary mechanism for the anticoagulant activity of heparin is mediated by the terminal pentasaccharide sequence at the non-reducing end of the Heparin (GlcNAc/NS(6S)-GlcA-GlcNS(3S,6S)-IdoA (2S)-GlcNS(6S), Molecular weight 1.7 KD).

Via their terminal pentasaccharide, Heparins bind to enzyme inhibitor antithrombin III, causing a conformational change that results in its activation through an increase in the flexibility of its reactive site loop. The activated antithrombin in turn inactivates thrombin, factor Xa or other proteases involved in the catalysis of coagulation-related reactions. The inhibition of factor Xa is mediated by conformational change in the antithrombin upon heparin-binding. For thrombin inhibition, the formation of a ternary complex between antithrombin III, thrombin, and heparin is however necessary. While heparin activity on factor Xa solely relies on the binding site of the terminal pentasaccharide, the activity of heparin on thrombin exhibits in addition a size dependence.

The size dependence has been exploited to allow for a reduced and thus more controlled regulation of coagulation by developing low-molecular-weight heparins (LMWHs) as pharmaceutical anticoagulants. More recently, a synthetic version of the terminal pentasaccharide of Heparin, referred to as Fondaparinux has been generated as a further anticoagulant.

In contrast to unfractionated heparin (UVH), both LMWHs as well as Fondaparinux are characterized by an anti-Xa activity rather than an antithrombin activity, reducing the risk of heparin-induced thrombocytopenia.

However, as with any anticoagulant unfractionated heparin (UVH), LMWHs or Fondaparinux may induce as severe side effects hemorrhage, including gastrointestinal bleeding and intracranial hemorrhage (Harter et al. 2015).

The inventor has realized that the terminal pentasaccharide sequence of Heparin in negatively charged glycosaminoglycan is unnecessary for the inhibition of tumour proliferation by disrupting the platelet-cell surface interaction. Advantageously, a combined administration of a negatively charged glycosaminoglycan that is characterized by the absence of the terminal pentasaccharide of Heparin, together with an inhibitor of the MAPK/ERK pathway, allows for a cancer treatment without the risk of anticoagulant side effects, such as hemorrhage.

The combined administration as described herein is thus particularly advantageous for patients afflicted with a cancerous disease, but at risk of developing hemorrhage in case of an anticoagulant administration. The combined administration is particularly useful for tumour patients for which an anticoagulant therapy is not medically indicated and would unnecessarily augment the risk of side affects associated with such a therapy.

In a one embodiment of the invention, negatively charged glycosaminoglycans are administered that substantially or essentially lack an anticoagulant activity, show a reduced anticoagulant activity compared to unfractionated heparin or to LMWH.

In one embodiment of the invention, the glycosaminoglycan for use as a medicament is characterized in that the terminal pentasaccharide of Heparin, which is absent, is the pentasaccharide GlcNAc/NS(6S)-GlcA-GlcNS(3S,6S)-IdoA(2S)-GlcNS(6S).

In one embodiment of the invention, the negatively charged glycosaminoglycan characterized by the absence of the terminal pentasaccharide of Heparin is a sulfated glycosaminoglycan such as pentosan polysulfate (PPS), dextran sulfate (DXS), a chondroitin sulfate, dermatan sulfate or a Keratan sulfate.

Varying degrees of sulfation occur in both naturally occurring and synthetic sulfated glycosaminoglycans. In a preferred embodiment the sulfated glycosaminoglycans may be selected, or modified, for particular degrees of sulfation in order to enhance the technical effect described herein.

As known in the prior art, sulfation causes a molecule to become negatively charged. Highly sulfated glycosaminoglycans, and hence more negatively charged sulfated glycosaminoglycans, are in some embodiments more effective in inhibiting the platelet-cell interaction than lowly sulfated, and hence less negatively charged, sulfated glycosaminoglycans. Relatively higher levels of sulfation can therefore augment the therapeutic effect. Furthermore, a highly sulfated glycosaminoglycans are typically able to block several such receptor molecules at once and will have a higher chance of being bound before it is diluted or washed away with body fluids.

The degree of sulfation of the sulfated glycosaminoglycans may be preferably about 0.5, 0.6, 0.7, 0.8, 0.9, 1.0, 1.1, 1.2, 1.3, 1.4, 1.5, 1.6, 1.7, 1.8, 1.9, 2.0, or more than 2.0.

In one embodiment of the invention the glycosaminoglycan for use as a medicament is a sulfated glycosaminoglycan, wherein the degree of sulfation is >1.0, preferably >1.2, more preferably >1.4. Sulfated glycosaminoglycans with a degree of sulfation >1.0, preferably >1.2, more preferably >1.4, are typically regarded as highly sulfated.

As described below, the degree of sulfation of any given glycosaminoglycan can be adjusted using methods known to those skilled in the art. The degree of sulfation can also be determined with appropriate experimentation, thereby enabling a skilled person to adjust the degree of sulfation in order to produce a glycosaminoglycan that exhibits optimal properties for the intended use. Commercially available or naturally obtained glycosaminoglycan molecules could therefore be modified to adjust the respective degree of sulfation accordingly.

In one embodiment of the invention, the glycosaminoglycan characterised by the absence of the terminal pentasaccharide of Heparin for use as a medicament as described herein is pentosan polysulfate (PPS).

In one embodiment of the invention, the glycosaminoglycan characterised by the absence of the terminal pentasaccharide of Heparin for use as a medicament as described herein is dextran sulfate (DXS).

Both sulfated glycosaminoglycan PPS and DXS exhibit remarkable inhibitory effects on the platelet-cell interaction and are thus particularly suited to yield a beneficial therapeutic effect, when combined with the administration of a MAPK/ERK inhibitor.

In a preferred embodiment of the invention the glycosaminoglycan characterised by the absence of the terminal pentasaccharide of Heparin, preferably exhibits a molecular weight of 1000 to about 500 000 daltons, preferably 2000 to 100 000 daltons, more preferably from about 5000 to about 12 000 daltons, or essentially the same approximate molecular weight as the low molecular weight heparin molecules (LMWH) known in the prior art and disclosed herein. Glycosaminoglycans from about 5000 to about 12000 daltons molecular may be termed low molecular weight glycosaminoglycans.

In a further embodiment of the invention the glycosaminoglycan characterised by the absence of the terminal pentasaccharide of Heparin, such as DXS or PPS, has a molecular weight of from about 2 kDa to about 12 kDa, more preferably about 3 kDa to about 8 kDa, most preferably of about 4 kDa to about 6 kDa. The low molecular weight glycosaminoglycans as described herein (about 2 kDa to about 12 kDa, preferably under 8 kDa) are characterised by additional advantages in comparison to unfractionated or high molecular weight glycosaminoglycans. The low molecular weight glycosaminoglycans typically lead to lower amounts of platelet aggregates than unfractionated or high molecular weight preparations. Through the administration of such relatively low molecular weight preparations the complication of a thrombosis during treatment is significantly reduced.

The glycosaminoglycans characterised by the absence of the terminal pentasaccharide of Heparin, enable reduced risk of both thrombocytopenia (potentially caused by Heparin associated immune thrombocytopenia; HIT, Type II) and thrombosis (unwanted clotting). Although these two complications appear to be due to contrasting mechanisms, either may occur during treatment with unfractionated glycosaminoglycans comprising the terminal pentasaccharide of Heparin, such as unfractionated heparin. Unfractionated heparin can therefore reduce platelet numbers too strongly, or can lead to platelet aggregation, either of which may lead to dangerous side effects. Surprisingly, PPS and DXS both show beneficial properties that enable the avoidance of these effects.

In one embodiment, the molecular weight of the relevant glycosaminoglycan can be determined using mass spectrometry-based method, such as is described in Rhomberg et al. 1998. The particular saccharide structure and further information on sulfation and molecular weight can be determined using sequencing techniques disclosed in Turnbull et al. 1999.

In one embodiment of the invention, the inhibitor of the MAPK/ERK pathway for the combined administration as described herein is a MEK Inhibitor.

Preferably the MEK inhibitor is selected from a group consisting of AZD8330 (ARRY-424704), Refametinib (BAY 86-9766, RDEA119), Cobimetinib (GDC-0973, XL-518, RG7421); E6201; Binimetinib (MEK162, ARRY-162); PD0325901; Pimasertib (AS703026, MSC1936369B); R04987655 (CH4987655), R05126766 (CH5126766), Selumetinib (AZD6244, ARRY-142,886); TAK-733; Trametinib (GSK1120212), GDC-0623, PD035901, PD184352 (CI-1040) and WX-554. Also the MEK inhibitor may be selected from the group consisting of U0126-EtOH, PD98059, BIX 02189, Pimasertib (AS-703026), BIX 02188, AZD8330 and PD318088, Honokiol, SL-327, Refametinib (RDEA119, Bay 86-9766), GDC-0623 and APS-2-79 HCl.

It is particularly preferred that the MEK inhibitor is selected from a group consisting of Trametinib (GSK1120212), Cobimetinib or XL518, Binimetinib (MEK162), PD325901, PD184352 (CI-1040), PD035901, and TAK-733.

In one embodiment of the invention the MEK inhibitor is Selumetinib.

As used herein, the names in the brackets denote preferably alternative nomenclature for the inhibitors.

In single-therapeutic studies some MEK inhibitors exhibit reduced therapeutic activity or increased side effects, if the dose is augmented in order to be therapeutically effective.

Advantageously the combined administration of the MEK inhibitor with the negatively charged glycosaminoglycan according to the invention allows for a lower dose regime, while maintaining a therapeutic effect.

The administration of a MEK inhibitor for the treatment of cancer is particularly preferred in combination with the negatively charged glycosaminoglycans PPS and/or DXS.

In one embodiment of the invention the glycosaminoglycan for use as a medicament in a combined administration as described herein is characterised in that the cancer to be treated is an ovarian cancer, a melanoma, preferably a metastatic melanoma, an advanced melanoma carrying a BRAF V600E or V600K mutation or NRAS Q61 mutant melanoma, an ovarian cancer, a breast cancer, a colon cancer or a lung cancer, preferably a non-small cell lung cancer (NSCLC). It is particular preferred that for the aforementioned types of cancer the inhibitor of the MAPK/ERK pathway is a MEK inhibitor.

In a one embodiment of the invention the inhibitor of the MAPK/ERK pathway for the combined administration as described herein is a Raf inhibitor.

Preferably the Raf inhibitor is selected from a group consisting of vemurafenib (PLX4032, RG7204), Sorafenib Tosylate, PLX-4720, Dabrafenib (GSK2118436), GDC-0879, CCT196969, RAF265 (CHIR-265), AZ 628, NVP-BHG712, SB590885, ZM 336372, Sorafenib, GW5074, TAK-632, CEP-32496, Encorafenib (LGX818), RO5126766 (CH5126766), MLN2480, PLX7904, CCT196969 and LY3009120.

It is particularly preferred that the Raf inhibitor is selected from a group consisting of Encorafenib (LGX818), Dabrafenib (GSK2118436) and vemurafenib (PLX4032).

In one embodiment of the invention, the inhibitor of the MAPK/ERK pathway for the combined administration is a Raf inhibitor and the cancer to be treated is a melanoma, thyroid cancer or a colon cancer.

In one embodiment, the invention relates to a combined administration of a negatively charged glycosaminoglycan as described herein together with a tyrosine kinase inhibitor in the treatment of cancer. Preferably such tyrosine kinase inhibitor is a receptor tyrosine kinase inhibitor that interferes with the MAPK/ERK pathway by impeding the function of the initial activation of a receptor tyrosine kinase (RTK).

In one embodiment the tyrosine kinase inhibitor is selected from a group consisting of Afatinib, Aflibercept, Axitinib, Bevacizumab, Bosutinib, Cabozantinib, Crizotinib, Dasatinib, Erlotinib, Gefitinib, Imatinib, Lapatinib, Nilotinib, Panitumumab, Pazopanib, Pegaptanib, Ponatinib, Ranibizumab, Regorafenib, Ruxolitinib, Sorafenib, Sunitinib, Tofacitinib, Trastuzumab and Vandetanib.

In one embodiment, the invention relates to the combined administration of a negatively charged glycosaminoglycan as described herein together with two or more inhibitors of the MAPK/ERK pathway. For instance it may be preferred that a negatively charged glycosaminoglycan is administered in combination with a MEK inhibitor and a RAF inhibitor.

In a preferred embodiment, the invention relates to a glycosaminoglycan for use as a medicament, wherein the cancer to be treated comprises cancerous cells that are resistant to and/or at elevated risk of developing resistance to an inhibitor of the MAPK/ERK pathway, in particular to a MEK Inhibitor and/or a Raf Inhibitor.

As described above, when treating cancerous diseases associated with aberrant activity of the MAPK/ERK signalling pathway with MAPK/ERK pathway inhibitors such as MEK inhibitors or Raf inhibitors, the occurrence of adaptive escape mechanisms are observed, which lead to a resistance of the cancer to the treatment. The treatment of such cancers may benefit in particular from a combined administration of a MAPK/ERK pathway inhibitor and a negatively charged glycosaminoglycan as described herein.

A person skilled in the art will know how to identify cancerous cells or cancers that are resistant to and/or at elevated risk of developing resistance to an inhibitor of the MAPK/ERK pathway. Such an identification involves preferably two aspects. In a first aspect it is determined whether the cancerous cells exhibit an aberrant e.g. elevated activity of the MAPK/ERK pathway in comparison to normal (non-cancerous) cells. An aberrant activity of the pathway can be deduced for instance from an overexpression and/or mutation of key members of the MAPK/ERK pathway, including RAS, MEK or Raf genes. For types of cancers that exhibit aberrant activity of the MAPK/ERK pathway, a specific inhibitor of said pathway may be expected to be a promising therapeutic target. However, as stated above, escape routes may lead to a resistance to a single-MAPK/ERK pathway inhibitor therapy. In a second aspect, it is therefore identified whether the cancer or cancerous cells are resistant, or at risk of developing a resistance to the inhibitor of the MAPK/ERK pathway, in particular to a MEK Inhibitor and/or a Raf Inhibitor.

To this end a person skilled in the art is aware of suitable in vitro and/or in vivo assays. For instance, an in vitro assay may include the application of the MEK inhibitor to the cancerous cells and subsequently monitoring effects on cell cycle and/or cell proliferation in comparison to suitable controls. Such in vitro assays may further include a control assay to assess whether the MAPK/ERK pathway inhibitor is functioning at the applied dose by monitoring the expected effect on a direct downstream target. For instance in case of a potent MEK inhibitor, phosphorylation of the downstream ERK is expected to be reduced. If cell proliferation and/or cell cycle of the cancerous cells are nevertheless uncompromised, a parallel signalling pathway is likely activated in the development of a resistance. In vitro assays may therefore also include monitoring if the MAPK/ERK pathway inhibitor activates alternative signalling pathways in support of cell proliferation. For instance, an upregulation of Erb-family protein signalling has been observed in the development of a resistance towards MAPK/ERK pathway inhibitions. An elevation of Erb-family protein signalling in cancerous cells in response to MAPK/ERK pathway inhibitors may therefore also indicate the development of resistance. Furthermore, a person skilled in the art also knows in vivo assays to monitor the resistance or development of resistance including monitoring of tumour growth in suitable model organisms in response to a MAPK/ERK pathway inhibitor administration. Moreover a person skilled in the art may rely on literature or clinical data reporting the development of resistance to MAPK/ERK pathway inhibitors in particular cancer types as disclosed e.g. in McCubrey et al. 2007, Rosen et al. 2013 and Poulikakos P. I. et al. 2011.

Resistance of cancerous cells to a MAPK/ERK pathway inhibitor is observed in particular in cancerous cells that exhibit an elevated presence or activity of one or more ErbB-family proteins, e.g. EGFR or ErbB3.

Additionally, the detection and/or quantification of mRNA encoding the enzymes involved in a particular signalling pathway may be used to detect whether cancerous cells exhibit an aberrant e.g. elevated activity of the MAPK/ERK pathway in comparison to normal (non-cancerous) cells. The selection of suitable enzymes, pathway members, mRNA sequences and particular primers may be selected by a skilled person without undue effort.

Therefore, in one embodiment the invention relates to the glycosaminoglycan for use as a medicament in a combined administration as described herein, wherein the cancer comprises cancerous cells that exhibit the presence of one or more ErbB-family proteins on the cell surface. The combined administration of a negatively charged glycosaminoglycan together with an inhibitor of the MAPK/ERK signalling pathway is therefore particularly beneficial for cancerous cells that exhibit elevated basal levels of ErbB-family proteins or that develop elevated signalling levels of ErbB-family proteins in response to a MAPK/ERK pathway inhibitor treatment.

Therefore, in one embodiment the invention relates to the glycosaminoglycan for use as a medicament in a combined administration as described herein, wherein the cancer comprises cancerous cells that exhibit increased expression (up-regulation) of one or more ErbB-family proteins and/or increased ErbB signalling compared to an appropriate (non-cancerous) control cell.

In a preferred embodiment the up-regulated ErbB-family protein is Her1 (EGFR, ErbB1), Her2 (Neu, ErbB2), Her3 (ErbB3), or Her4 (ErbB4), most preferably the up-regulated ErbB-family protein is Her3 (ErbB3).

Since the negatively charged glycosaminoglycan directly inhibits cell surface contacts with the platelets, in a preferred embodiment the invention relates to a local administration of said negatively charged glycosaminoglycan to regions in proximity to tumour tissues.

The local administration of negatively charged glycosaminoglycan to regions in proximity to tumour tissue enables lower doses of negatively charged glycosaminoglycan to be administered, that maintain an effective anti-proliferation effect with reduced systemic toxicity. In the meaning of the present invention, local administration relates to administration, for example via injection, transmucosal or transdermal approaches, to a region within preferably 10 cm, within 5 cm, or preferably within 1 cm to tumour tissue, or delivery within the tumour itself.

Methods of local administration may therefore relate to parenteral administration, such as intravenous (into a vein), intra-arterial (into an artery), intraosseous infusion (into the bone marrow), intra-muscular, intracerebral (into the brain parenchyma), intracerebroventricular (into cerebral ventricular system), intrathecal (an injection into the spinal canal) or subcutaneous (under the skin) administration.

In the combined treatment the administration of the MAPK/ERK pathway inhibitor can also be local, preferably using an identical route as for the glycosaminoglycan, but may also be systematic, even if the glycosaminoglycan is administered locally.

In one embodiment local administration relates to intra-arterial administration into an artery responsible for providing blood to a tumour. Such an approach may be particularly relevant in cases where a particular organ or tissue may not be removed from the patient, even in cases where a tumour has developed. The local administration in this region via intra-arterial administration thereby provides a unique method of disrupting interaction between platelets and the cell surface of dividing cells, thereby providing a useful therapeutic effect.

In a further aspect the invention relates to pharmaceutical compositions for the treatment of cancers comprising the combined administration of a negatively charged glycosaminoglycan and a pharmaceutically acceptable carrier and a MAPK/ERK pathway inhibitor and a pharmaceutically acceptable carrier.

The negatively charged glycosaminoglycan and the MAPK/ERK pathway inhibitor may be administered together with a single pharmaceutical composition using the same pharmaceutically acceptable carrier. However, the negatively charged glycosaminoglycan and the MAPK/ERK pathway inhibitor may also be administered sequentially in separate pharmaceutical compositions and distinct pharmaceutical carriers.

DETAILED DESCRIPTION OF THE INVENTION

All cited documents of the patent and non-patent literature are hereby incorporated by reference in their entirety.

The present invention is directed to the treatment of a subject afflicted by cancerous disease(s) by means of a combined administration of a negatively charged glycosaminoglycan and an inhibitor of the MAPK/ERK pathway.

The term "subject" includes both human and veterinary subjects. The term "treatment" refers to a therapeutic intervention that ameliorates a sign or symptom of a disease or pathological condition after it has begun to develop. As used herein, the term "ameliorating", with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease.

The present invention encompasses both treatment and prophylactic treatment of a subject. A "prophylactic" treatment is a treatment administered to a subject who does not exhibit signs of a disease or exhibits only early signs for the purpose of decreasing the risk of developing pathology. In some embodiments, the invention therefore relates to the prevention or prophylaxis of cancer resistance to an inhibitor of the MAPK/ERK pathway.

The terms "in combination", "combined administration", "administered in combination" or the like as utilized herein are meant to encompass administration of the therapeutic agents in the treatment of the same disease or condition to a single patient selected, administering these agents using the same or different routes, or at the same time or at different times. The combined administration of the negatively charged glycosaminoglycan and the inhibitor of the MAPK/ERK pathway is thus to be understood as the use of the two or more active agents administered in separate formulations or a single pharmaceutical formulation or consecutive administration in any order, such that both (or all) active agents simultaneously exert their biological activity over a period of time. The glycosaminoglycan and the inhibitor of the MAPK/ERK pathway need not be administered in combination at the same time at the same frequency or administered by the same route of administration. In some embodiments, they are administered sequentially within about 60, 30, 15, 10, 5, or 1 minute of one another. In some embodiments, they are administered sequentially within about 1 hour, 5 hours, 1 day, 1 week or 1 month of one another. It is intended to include treatment regimens of ongoing treatment, and multiple administration events.

The present invention relates also to a pharmaceutical composition comprising a negatively charged glycosaminoglycan and an inhibitor of the MAPK/ERK pathway. Alternatively, the present invention relates also to the employment of multiple pharmaceutical compositions comprising, separately, a negatively charged glycosaminoglycan and an inhibitor of the MAPK/ERK pathway. The pharmaceutical composition comprises preferably one or more pharmaceutically acceptable carriers. As used herein, "pharmaceutically acceptable carrier" means any of the various carriers known to those skilled in the art. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrrolidone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbonyl and polyvinylpyrrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

The invention therefore provides a method for orally delivering the glycosaminoglycan and/or the inhibitor of the MAPK/ERK pathway to a subject comprising administering to the subject a pharmaceutically effective amount of one of the above-mentioned pharmaceutical compositions.

The pharmaceutical composition(s) of the present invention is/are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, and mode of administration and has to be determined in preclinical and clinical trials for each respective indication.

Dosage levels of approximately 0.01 mg to about 500 mg of the negatively charged glycosaminoglycan and approximately 0.01 mg to about 500 mg of the inhibitor of the MAPK/ERK pathway per kilogram of body weight per day are useful in the treatment of the above-indicated conditions. For example, cancerous diseases may be effectively treated by the combined administration of about 0.01 to 100 mg of each of the compounds per kilogram of body weight per day (about 0.5 mg to about 3.5 g per patient per day). The amount of active ingredients that may be combined with the carrier materials to produce a single dosage form will vary depending upon the host treated and the particular mode of administration. For example, a formulation intended for the oral administration in humans may vary from about 1 to about 95% of the total composition. Dosage unit forms will generally contain between about 1 mg to about 500 mg of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount for the negatively charged glycosaminoglycan will range from about 0.0001 mg/kg to 1500 mg/kg, more preferably 1 to 1000 mg/kg, more preferably from about 1 to 150 mg/kg of body weight, and most preferably about 10 to 100 mg/kg of body weight, when administered in combination with a dosage of the inhibitor of the MAPK/ERK pathway in an amount from about 0.0001 mg/kg to 1500 mg/kg, more preferably 1 to 1000 mg/kg, more preferably from about 1 to 150 mg/kg of body weight, and most preferably about 10 to 100 mg/kg of body weight.

Animal models conducted with PPS administration have typically used between 10 and 30 mg/kg body weight PPS during treatment for enhanced allograft survival, for example in Schwartz et al. 1999.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

In connection with the present invention, the terms "cell growth" and "proliferation" are both used, and may be used interchangeably. In medicine, especially in oncology, the term cell growth is frequently used with respect to the increase in cell number (e.g. due to tumour growth). Tumour growth is caused by increased proliferation of tumour cells. Cell growth, on a scale and increase in volume of a single cell is also included within this definition. In a preferred embodiment, the invention relates to modulation of cell proliferation, in particular of cancerous cells. Cell growth or cell proliferation can be distinguished from the metastasis of tumour cells, which relates to the migration (change in location) of cells. Metastasis and proliferation represent different aspects of a tumour and can be viewed as different clinical indications.

According to the present invention "cancer" or "proliferative disorder" as used herein is a group of proliferative diseases or disorders characterized by the uncontrolled growth and/or spread of malignantly altered endogenous cells.

Cancer as used herein may relate to any given carcinoma, such as those arising from ectodermal tissues i.e. cancer of the skin, breast, nervous system and such as those arising from mesodermal tissue i.e. cancer of bone, cartilage, muscle, kidney, lymphoma or leukemia, germ cell tumours, and those arising from endodermal tissues i.e. cancer of the liver, pancreas, thyroid gland, lung, stomach, bowel and bladder, caused by alterations in the growth control mechanisms of the tissues affected.

Examples of cancer include, but are not limited to Hodgkin's disease, non-Hodgkin's lymphoma, acute lymphocytic leukemia, multiple myeloma, neuroblastoma, breast carcinoma, ovarian carcinoma, lung carcinoma, Wilms' tumour, testicular carcinoma, soft-tissue sarcoma, bladder carcinoma, chronic granulocytic leukemia, primary brain carcinoma, malignant melanoma, small-cell lung carcinoma, stomach carcinoma, colon carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, renal cell carcinoma, endometrial carcinoma, essential thrombocytosis, adrenal cortex carcinoma, skin cancer, and prostatic carcinoma. Furthermore, specific cellular proliferation disorders are encompassed by the present invention, such as, for example, benign prostate hyperplasia, familial adenomatosis polyposis (FAP), psoriasis, vascular smooth cell proliferation associated with atherosclerosis, pulmonary fibrosis, hyperkeloidosis, glomerulonephritis and post-surgical stenosis and restenosis.

The term "cancerous cell" as provided herein, includes a cell afflicted by any one of the above-identified conditions.

Other disorders associated with unwanted cell proliferation relate, without limitation, to auto-immune diseases. The invention therefore further relates to a negatively charged glycosaminoglycan for use as a medicament in the treatment of a disease associated with unwanted cell proliferation, such as an autoimmune disease, comprising the combined administration of (1) a negatively charged glycosaminoglycan, wherein said glycosaminoglycan is characterised by the absence of the terminal pentasaccharide of Heparin, and (2) an inhibitor of the MAPK/ERK pathway.

The pathogenesis of many diseases is associated with cell growth. As an example, an unwanted immune response is one such disease. An immune response leads to proliferation of one or a few concerned cell clones by the immune system in order to produce further immune cells or antibodies to the causative agent. In cases of unwanted or pathogenic immune responses, the effector cells of the immune system, or antibodies produced by the immune system, may be directed against the body's own tissues, leading to autoimmunity. These immune reactions lead to significant tissue damage. This damage causes the disease symptoms of the autoimmune disease.

According to the present invention an "autoimmune disorder" or "autoimmune disease" as used herein is a group of diseases or disorders arising from a pathological immune response, either humoral or cellular or both, directed against an individual's own tissues and condition resulting therefrom.

Examples of autoimmune diseases or disorders include, but are not limited to acute and chronic rheumatoid diseases such as rheumatic fever, rheumatoid arthritis, osteoarthritis, psoriatic arthritis, and ankylosing spondylitis, Sjögren's syndrome, Stevens-Johnson syndrome, acute and chronic autoimmune diseases of the skin such as urticaria, dermatomyositis, toxic epidermal necrolysis, scleroderma, multiple sclerosis, pyoderma gangrenosum, erythema nodosum, systemic lupus erythematosus (SLE), allergic conditions, such as asthma, and autoimmune gastrointestinal and endocrine disorders such as ulcerous colitis, Crohn's disease, diabetes mellitus, Hashimotos thyroiditis, autoimmune dilatative myocarditis, autoimmune vasculitis such as thrombangitis obliterans, and myositis, autoimmune anemia and autoimmune forms of myelophtisis, idiopathic thrombocytopenic purpura (ITP) and autoimmune diseases of the kidneys such as acute and chronic glomerulonephritis.

The invention also relates to a process or a method for the treatment of the above mentioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions.

The term "physical interaction between platelets (thrombocytes) and cancerous cells" relates to any given physical interaction or binding between platelets and the cell surface of said cancerous cells of greater frequency or strength than would occur by chance when said platelets and quiescent cells are present together in vitro. In a preferred embodiment said interaction can be defined and interrogated via carrying out the methods described in WO 2015/059177A1, such as co-culture or incubation, washing (preferably 2 to 4 times) and subsequent fixing and identification. As described herein, an administration of negatively charged glycosaminoglycans allows to interfere and/or inhibit the physical interaction between platelets and cancerous cells.

The term "glycosaminoglycan", as used herein, refers to an oligo- or polysaccharide, comprising preferably aminohexose units. The term "negatively charged glycosaminoglycan" is preferably used as in the state of the art referring to glycosaminoglycans that are anionic and exhibit a negative charge at a neutral pH value. Sulfated glycosaminoglycans are a particularly preferred group of negatively charged glycosaminoglycans. Sulfated glycosaminoglycans include, but are not limited to, chondroitin sulfate, dermatan sulfate, keratan sulfate, heparin, heparan sulfate, pentosan polysulfate (PPS) and dextran polysulfate (DXS). Unsulfated glycosaminoglycans that are negatively charged include, but are not limited to hyaluronic acids.

The term "negatively charged glycosaminoglycan characterised by the absence of the terminal pentasaccharide of Heparin" preferably refer to negatively charged glycosaminoglycans that lack GlcNAc/NS(6S)-GlcA-GlcNS(3S,6S)-IdoA(2S)-GlcNS(6S). Examples of "negatively charged glycosaminoglycan characterised by the absence of the terminal pentasaccharide of Heparin" include but are not limited to chondroitin sulfate, dermatan sulfate, keratan sulfate, hyaluronic acid, pentosan polysulfate (PPS) and dextran polysulfate (DXS).

The term "heparin" includes unfractionated heparin and heparins having a lower molecular weight. In one embodiment, the heparin used in accordance with this invention is "unfractionated heparin" (UFH) which may have an average molecular weight of about 8 kDa to about 30 kDa, preferably of about 10 kDa to about 20 kDa, most preferably of about 12 kDa to about 16 kDa, e.g. about 15 kDa.

The term "heparin" includes also small molecular weight fragments of heparin molecules, either derived from naturally occurring heparin by cleavage and isolation or by synthetic routes.

As described herein the term low molecular weight heparin (LMWH) preferably refers to heparins or heparin salts having an average molecular weight of less than 8000 Da and for which at least 60% of all chains have a molecular weight less than 8000 Da. Low molecular weight heparin is a term commonly accepted in the art and requires no further clarification for a skilled person. LMWH do not cause thrombocytopenia as frequently as UFH. Their ability to bind platelets is substantially reduced.

Preferably, the molecular weight of the LMWH used in accordance with this invention is about 2 kDa to about 8 kDa, more preferably about 3 kDa to about 6 kDa, most preferably of about 4 kDa to about 5 kDa, e.g. about 4.5 kDa. The LMWHs can be obtained by various methods of fractionation or depolymerisation of polymeric heparin.

Examples of LMWHs include, but are not limited to, ardeparin (Normiflo), certoparin (Sandoparin), enoxaparin (Lovenox and Clexane), parnaparin (Fluxum), tinzaparin (Innohep and Logiparin), dalteparin (Fragmin), reviparin (Clivarin) and nadroparin (Fraxiparin).

As used herein, the term "degree of sulfation" refers to the number of sulfate groups (—OSO3) per monosaccharide unit. Although degree of sulfation may be provided in other sources of literature as the number of sulfate groups (—OSO3) per disaccharide unit, the definition of the present invention relates to the number of sulfates per monosaccharide unit. Some GAGs exist not as disaccharide polymers but as monosaccharide polymers. In order to provide a consistent degree of sulfation measurement, the degree of sulfation per monosaccharide unit is used and the degrees of sulfation for disaccharide units are adjusted accordingly.

Sulfation of any given polysaccharide or GAG may be modified according to the saccharide sulfation methods described in US 20050119469 A1, which is hereby incorporated in its entirety by reference.

The degree of sulfation may be determined by techniques known to those in art, such as those disclosed in Zaia et al. (BioMed Research International, Volume 2014 (2014), Article ID 986594) or other related methods using mass spectrometry analysis.

Heparin shows higher degree of sulfation (1-3 sulfates/monosaccharide, preferably 1.5, or 2) when compared to heparan sulfates (0.3-0.7) sulfates/monosaccharide.

TABLE 1

Glycosaminoglycans and sulfation degree (amended from Wang et al. 2012).

| GAG | Sugar 1 | Sulfates | Sugar 2 | Sulfates | Degree of Sulfation |
|---|---|---|---|---|---|
| hyaluronan | GlcNAc | none | GlcA | none | 0 |
| chondroitin | GalNAc | none | GlcA | none | 0 |
| chondroitin sulfate | GalNAc | 4S or 6S | GlcA | none | 0.5 |
| dermatan sulfate | GalNAc | 4S | IdoA or GlcA | none | 0.5 |
| heparaosan | GlcNAc | none | GlcA | none | 0 |
| heparan sulfate | GlcNAc or NS | none or 6S or 3S | GlcA | none or 2S | 0.5 |
| heparin | GlcNS or GlcNAc | 6S ± 3S | IdoA or GlcA | 2S | 1.5 |
| N-sulfo heparosan | GlcNS | none | GlcA | none | 0.5 |
| undersulfated heparin | GlcNS or GlcNAc | none or 6S or 3S | GlcA or IdoA | none or 2S | 1 |

The degree of sulfation in Table 1 is the average number of sulfates in the monosaccharide unit of each GAG. Although the GAGs shown are disaccharide GAGs, the degree of sulfation has been adjusted for a monosaccharide GAG. Abbreviations are: GlcNAc, N-acetyl-α-D-glucosamine; GalNAc, N-acetyl-β-D-galactosamine; GlcNS, N-sulfo-α-D-glucosamine; GlcA, β-D-glucuronic acid; α-L-IdoA iduronic acid; and S, sulfo.

Pentosan polysulfate (PPS), for example sold under the name Elmiron, by Ortho-McNeil Pharmaceutical is an oral medication approved by the U.S. Food and Drug Administration (FDA) for the treatment of interstitial cystitis (IC), also known as painful bladder syndrome and under the names of Fibrezym® and Pentosanpolysulfat SP54® by bene Pharma. In the veterinary field, pentosan polysulfate is sold under the name Cartrophen Vet by Biopharm Australia. PPS is also sold under the names Naturevet Equine and Arthropen. The anticoagulant activity of PPS is 1/15 that of Heparin. PPS is a highly sulfated semisynthetic polysaccharide possessing a higher negative charge density and degree of sulfation than heparin. Like other glycosaminoglycans, the structural and chemical properties of PPS promote binding of the drug to the endothelium. PPS typically exhibits a degree of sulfation greater than 1.5 sulfate group per glucosyl residue.

Dextran sulfate (DXS) is a polyanionic derivative of dextran produced by esterification of Dextran with chlorosulphonic acid. DXS is a branched-chain polysaccharide polymer of d-glucose that is permeable to water and forms a viscid gelatinous material. The sulfur content is approximately 17% which corresponds to an average of 1.9 sulfate groups per glucosyl residue of the dextran molecule.

As used herein, the term "anticoagulant" is intended to mean any compound that has the ability, either directly or indirectly, to prevent the coagulation of blood or to dissolve blood clots. In a preferred embodiment the invention relates to glycosaminoglycans that substantially lack an anticoagulant activity. Substantially lacking an anticoagulant activity preferably refers to compounds that exhibit reduced activity on antithrombin III and/or factor Xa, e.g. having an antithrombin III activity of less than 50 IU/mg and/or an anti-Xa activity of less than 50 IU/mg.

As used herein, the term "inhibitor" is meant to describe a compound that blocks or reduces an activity of an enzyme. An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. As used herein an inhibitor may be a polypeptide, nucleic acid, carbohydrate, lipid, small molecular weight compound, an oligonucleotide, an oligopeptide, siRNA, antisense, a recombinant protein, an antibody, a peptibody, or conjugates or fusion proteins thereof. For a review of siRNA see Milhavet O. et al. 2003. For a review of antisense see Opalinska J B et. al. 2003.

A small molecular weight compound refers to a compound with a molecular weight of less than 2000 Daltons, 1000 Daltons, 700 Daltons or 500 Daltons.

"An inhibitor of the MAPK/ERK pathway" preferably refers to an inhibitor against the biological activity of wild-type or any mutant form of any of the enzymes involved in the MAPK/ERK pathway. As used herein, the term "MAPK/ERK pathway" or "MAPK/ERK signalling pathway", refers to a signal transduction pathway involving MAPK, MEK and ERK mitogen activated kinases, coupling intracellular responses to the binding of growth factors to cell surface receptors. The term MAPK/ERK pathway signalling pathway includes the many protein components and kinase cascades that are part of the signalling pathway, as well as the various targets regulated by the pathway.

The MAPK/ERK pathway is in the literature also referred to as the Raf-MEK-ERK pathway or Ras-Raf-MEK-ERK pathway. For a review of enzymes involved in the MAPK/ERK signalling pathway see for instance McCubrey J. A. et al. 2007.

The inhibitor of the MAPK/ERK pathway may include, without being limited to, an RTK inhibitor, a Ras inhibitor, a MEK inhibitor, a Raf inhibitor and/or an ERK inhibitor.

As used herein, "MEK" preferably refers to the mitogen-activated protein kinase kinase (also known as MAP2K, MAPKK) which is a kinase enzyme which phosphorylates mitogen-activated protein kinase (MAPK). The IUBMB Enzyme Nomenclature of MEK is EC 2.7.12.2. There are seven subtypes of MEK including MAP2K1 (MEK1), MAP2K2 (MEK2), MAP2K3 (MKK3), MAP2K4 (MKK4), MAP2K5 (MKK5), MAP2K6 (MKK6), MAP2K7 (MKK7). Most preferably as used herein the MEK is MEK1 or MEK2.

The term "MEK inhibitor" as used herein preferably refers to a compound that exhibits an 1050 with respect to MEK activity, of no more than about 100 µM or not more than about 50 µM as measurable by a MEK enzyme inhibitory assay described below. "1050" refers to the concentration of an inhibitor which reduces the activity of an enzyme (e.g., MEK) to half-maximal level.

Examples of MEK inhibitors include AZD8330 (ARRY-424704), Refametinib (BAY 86-9766, RDEA119), Cobimetinib (GDC-0973, XL-518, RG7421); E6201; Binimetinib (MEK162, ARRY-162); PD0325901; Pimasertib (AS703026, MSC1936369B); R04987655 (CH4987655), R05126766 (CH5126766), Selumetinib (AZD6244, ARRY-142,886), Trametinib (GSK1120212), GDC-0623, PD035901, PD184352 (CI-1040), WX-554, U0126-EtOH, PD98059, BIX 02189, BIX 02188, PD318088, Honokiol, SL-327, GDC-0623, APS-2-79 HCl, Cobimetinib, XL518, PD325901, TAK-733, R05126766 or HL-085.

However, the list of MEK inhibitors is not exhaustive and a person skilled in the art may determine whether a compound is a MEK inhibitor by known MEK enzyme inhibitory assay to determine the IC50 of the compound. One such assay is described for instance in U.S. Pat. No. 9,034,861 B2, the content of which is incorporated hereby in its entirety by reference.

MEK Enzyme Inhibitory Assay:

Materials and preparation of reagents: Purified recombinant full-length human GST-MEK1 are purchased from Cell Signaling Technology, Inc (Beverly, Mass., USA). MAP kinase substrate Erk1/Erk2 peptide are purchased from Enzo Life Sciences (Plymouth Meeting, Pa., U|S|A|).

Determination of enzymatic activity: Compounds are diluted three-fold in dimethylsulfoxide (DMSO) ranging from 1 mM to 1.37 µM concentration. A typical 20-microliter assay contained 80 ng MEK1, 4 µg Erk1/Erk2 peptide, 100 µM or 1 mM ATP, 1 µM to 1.37 nM test compound in 1× assay buffer containing 5 mM MOPS, pH 7.2, 2.5 mM β-glycerophosphate, 1 mM EGTA, 0.4 mM EDTA, 5 mM $MgCl_2$, 0.05 mM DTT. Enzyme reaction are incubated at room temperature for 90 minutes. At the end of kinase reaction, 20 µL of ADP-Glo reagent (Promega, Madison, Wis., USA) is added and incubated at room temperature for 40 minutes. Forty µL of kinase detection reagent (Promega) is added and incubated at room temperature for 1 h. Chemiluminescence is read and IC50s are calculated using Soft-Max software.

As used herein "Raf" refers to Raf kinases that are a family of serine/threonine-specific protein kinases including A-Raf, B-Raf or c-Raf (Raf 1).

The term "Raf inhibitor" or "Raf kinase inhibitor" as used herein refers to a compound that exhibits an IC50 with respect to Raf activity, of no more than about 100 µM or no more than about 50 µM measurable by an assay for determining 1050 values for a Raf protein kinase inhibitor as described below. "1050" refers to the concentration of an inhibitor which reduces the activity of an enzyme (e.g., Raf) to half-maximal level.

Examples of the Raf inhibitors include vemurafenib (PLX4032, RG7204), Sorafenib Tosylate, PLX-4720, Dabrafenib (GSK2118436), GDC-0879, CCT196969, RAF265 (CHIR-265), AZ 628, NVP-BHG712, SB590885, ZM 336372, GW5074, TAK-632, CEP-32496, Encorafenib (LGX818), R05126766 (CH5126766), MLN2480, PLX7904, CCT196969 and LY3009120.

However, the list of Raf inhibitors is not exhaustive and a person skilled in the art may determine whether a compound qualifies as a Raf inhibitor by known Raf kinase assays to determine the IC50 of the compound. One such assay is described for instance in WO 2009/018238 A, which content is incorporated in its entirety by reference.

Generation of Raf IC50 Data: A method for determining 1050 values for a Raf protein kinase inhibitor, e.g. sorafenib, in human cancerous cell lines is described in U.S. application Ser. No. 10/488,576, filed on Mar. 4, 2004, entitled "Pyridylfurans and pyrroles as Raf kinase inhibitors," and is hereby incorporated by reference in its entirety. Human diploid foreskin fibroblasts (HFF) or human colon carcinoma (Colo 201) cells are grown its Dulbecco's modified Eagle's medium (DMEM) (Invitrogen/Life Technologies) containing 10% fetal bovine serum (FBS) and the antibiotics penicillin (100 Units/ml) and streptomycin (100 micrograms/ml) (Invitrogen/Life Technologies). Growth is maintained at 37° C. in humidified 5% CO2 incubators in 75 cm 2 plastic flasks. Cells are harvested using 0.25% trypsin/1 mM ethylenediaminetetraacetic acid (EDTA), resuspended in growth medium, and counted using a hemocytometer. Flat-bottomed 96-well plates are seeded with, 2×10 3 cells/well in a volume of 200 ul from trypsinized exponentially growing cultures. To "blank" wells, growth medium is added with no additions. Cells will be incubated overnight to permit attachment.

Twenty-four hours later, medium from wells that contained cell's is replaced with 180 microliters of fresh medium. Appropriate dilutions of test compounds are added to the wells from stock solutions of Raf protein kinase compound dissolved in dimethyl sulfoxide (DMSO); final DMSO concentration in all wells was 0.2%. Cells plus compound are incubated for an additional 72 hr at 37° C. under normal growth conditions. Cells are then assayed for viability using standard XTT/PMS. Fifty microliters of XTT/PMS solution is added to each well and plates are incubated for 90 minutes at 37° C. Absorbance at 450 nM is then determined using a 96-well UV plate reader (Molecular Devices). Under these conditions, absorbance of untreated control cells at 450 nm is at least 1.0 optical density unit/ml. Percent viability of cells in each well is calculated from these data (having been corrected for background absorbance) which will be equal to 1000×(A450 test well/A450 untreated control well), wherein the A450s being averages of triplicate determinations, IC50 is determined based on that concentration of Raf kinase inhibitor compound that reduced cell viability to 50% of control (untreated) viability, as determined from plots of concentration vs percent viability.

As used herein, the term "receptor tyrosine kinase" or the abbreviation "RTK" is intended to mean any integral cell membrane-spanning protein capable of binding ligand in the wild-type form and possessing intrinsic tyrosine kinase activity. RTKs have a characteristic molecular architecture consisting of an extracellular region, a transmembrane domain which is typically a single transmembrane helix, and a cytoplasmic or intracellular region. The extracellular region may be composed of one or more domains that accommodate ligand binding. Such domains include but are not limited to: immunoglobulin domains, cysteine-rich domains, leucine-rich domains, fibronectin type III domains, kringle domains, ephrin binding domains, WIF domains, Sema domains, L domains. The cytoplasmic or intracellular (used herein interchangeably) region typically includes the tyrosine kinase domain (abbreviated to "TKD") and may additionally include a juxtamembrane regulatory region and/or a C-terminal region.

Twenty subfamilies of RTK have been described in humans including the EGF receptor family (ErbB family), the Insulin receptor family, the PDGF receptor family, the VEGF receptors family, the FGF receptor family, the HGF receptor family, the Trk receptor family, the Eph receptor family, the AXL receptor family, the LTK receptor family, the TIE receptor family, the ROR receptor family, the DDR receptor family, the RET receptor family, the KLG receptor family, the RYK receptor family and the MuSK receptor family.

As used herein, the term "ErbB-family protein" or "Erb protein" refers to one of the members of the ErbB family of receptors, also referred to as the EGFR family of receptors. As used herein, the ErbB-family proteins refer to a group of receptor tyrosine kinases including 1) HER-1, also known as the epidermal growth factor receptor (EGFR); 2) HER-2, also known as erbB2, c-neu, or p185; 3) HER-3, also known as erbB3; and 4) HER-4, also known as erbB4.

In preferred embodiments the invention relates to a combined administration of a negatively charged glycosaminoglycan together with an inhibitor of the MAPK/ERK pathway for the treatment of cancer, wherein the cancerous cells are characterized by an increased presence of ErbB-family proteins in comparison to control cells and/or an increased activity of ErbB-family proteins mediated signalling.

A number of methods known in the art can be used to assess whether the cancerous cells exhibit an elevated presence or activity of ErbB-family proteins. This may include the detection of levels of a protein, mRNA, or enzyme activity for the purposes of the present invention. For example, in some of the methods described herein, the level, presence or absence of protein, mRNA, or activity of an ErbB-family protein, such as EGFR or Erb3, is determined in a sample of the cancerous cells and compared to a control (e.g. non-cancerous) cell.

In some embodiments, the level of mRNA (transcript) can be evaluated using methods known in the art, e.g., Northern blot, RNA in situ hybridization (RNA-ISH), RNA expression assays, e.g., microarray analysis, RT-PCR, RNA sequencing (e.g., using random primers or oligoT primers), deep sequencing, cloning, Northern blot, and amplifying the transcript, e.g., using quantitative real time polymerase chain reaction (qRT-PCR). Analytical techniques to determine RNA expression are known. See, e.g., Sambrook et al, Molecular Cloning: A Laboratory Manual, 3rd Ed., Cold Spring Harbor Press, Cold Spring Harbor, N.Y. (2001).

Any method known in the art can be used for detecting the presence of proteins (e.g., using one or more antibodies that specifically bind to the protein of interest e.g. a protein of the Erb-family). For example, a sample can be contacted with one or more antibodies or antigenic portions thereof that specifically bind to the protein, e.g. an Erb-family protein; the binding of the one or more antibodies to proteins present in the sample can be detected using methods known in the art.

Methods for detecting binding of the antibodies to target proteins are known in the art, and can include the use of secondary antibodies. The secondary antibodies are generally modified to be detectable, e.g., labelled. The term "labelled" is intended to encompass direct labelling by coupling (i.e., physically linking) a detectable substance to the secondary antibody, as well as indirect labelling of the multimeric antigen by reactivity with a detectable substance. Examples of detectable substances include various enzymes, prosthetic groups, fluorescent materials, luminescent materials, bioluminescent materials, and radioactive materials. Examples of suitable enzymes include horseradish peroxidase (HRP), alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, and quantum dots, dichlorotriazinylamine fluorescein, dansyl chloride, and phycoerythrin; an example of a luminescent material includes luminol; examples of bioluminescent materials include green fluorescent protein and variants thereof, luciferase, luciferin, and aequorin; and examples of suitable radioactive material include $^{125}$I, $^{131}$I, $^{35}$S, or $^{3}$H. Methods for producing such labelled antibodies are known in the art, and many are commercially available.

Any method of detecting proteins present in a sample can be used, including but not limited to radioimmunoassays (RIA), enzyme-linked immunosorbent assays (ELISA), Western blotting, surface plasmon resonance, micro fluidic devices, protein array, protein purification (e.g., chromatography, such as affinity chromatography), mass spectrometry, two-dimensional gel electrophoresis, or other assays as known in the art.

Alternatively, an assay can comprise providing one or more nucleic acid probes that specifically bind to the mRNA encoding for the protein of interest, e.g. an Erb-family protein, contacting the nucleic acid probes with the sample comprising nucleic acids from the cancerous cell, and the binding of the probes to any mRNA encoding for the protein of interest, e.g. an Erb-family protein, present in the sample can be detected.

FIGURES

The following figures are presented in order to describe particular embodiments of the invention, by demonstrating a practical implementation of the invention, without being limiting to the scope of the invention or the concepts described herein.

SHORT DESCRIPTION OF THE FIGURE

Figure 2:
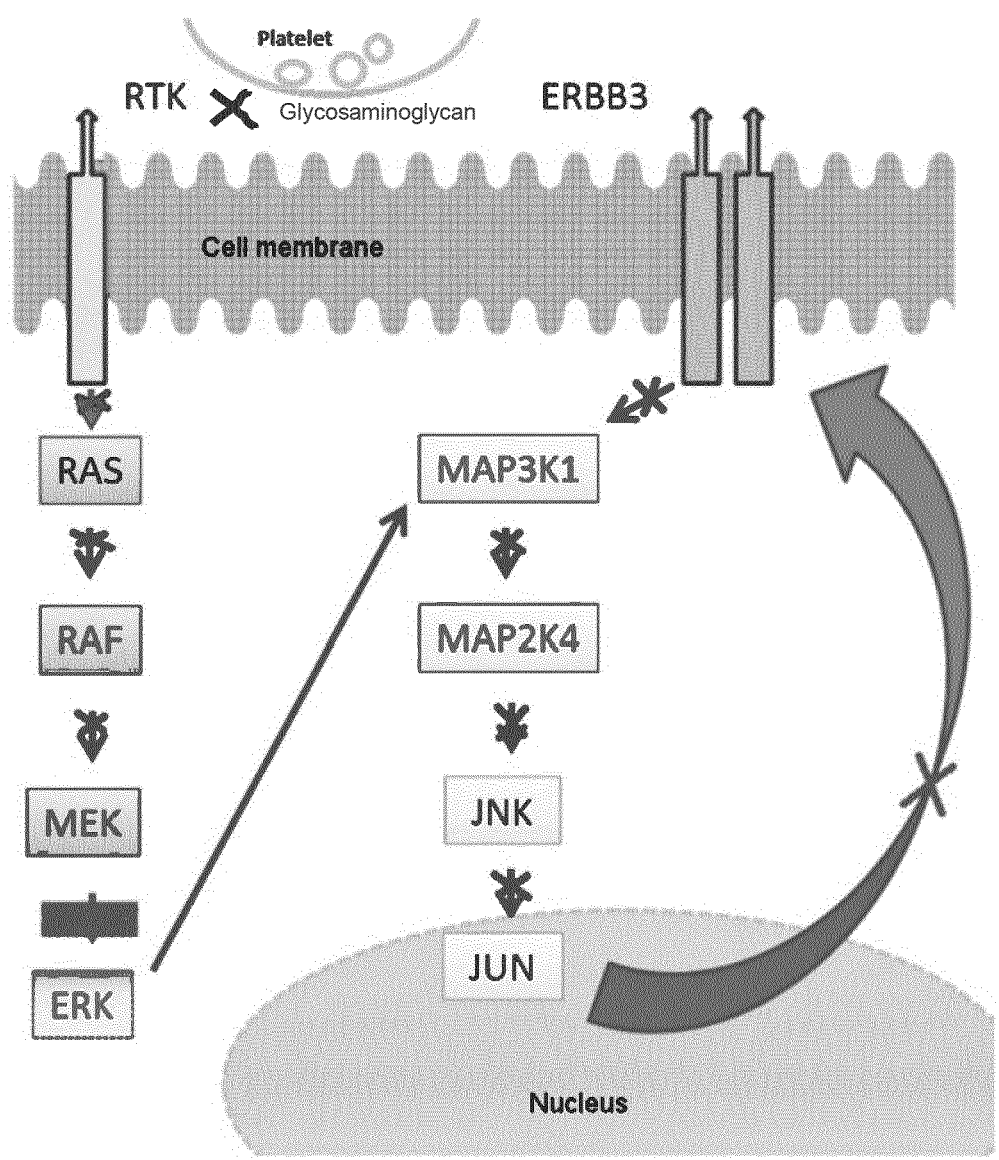

FIG. 1: Schematic illustration of a growth factor dependent escape mechanism leading to a MEK inhibitor resistance in cancerous cells.
FIG. 2: Schematic illustration of the benefit of an additional administration of a negatively charged glycosaminoglycan to prevent the development of a MEK inhibitor resistance in cancerous cells

DETAILED DESCRIPTION OF THE FIGURE

FIG. 1 illustrates of a growth factor dependent escape mechanism leading to an MEK inhibitor resistance in cancerous cells. In the MAPK/ERK pathway activation of a membrane bound RTK initiates a Ras tyrosine kinase chain leading to the activation of downstream transcription factors in support of cell proliferation. In this process platelets are involved. MEK inhibitors such as Selumetinib inhibit the phosphorylation and hereby also cell proliferation. However, tumours or cancerous cells treated with Selumetinib rapidly develop a resistance to the inhibitor. The resistance is likely caused by the fact that unphosphorylated ERK activates another tyrosine kinase chain, the depicted MAP3K1 pathway, which leads to a de novo synthesis of RTKs belonging to the HER family, e.g. ERBB3. The HER RTKs are activated by growth factors leading to MAP3K1 pathway signalling that enables the cell to bypass the compromised Ras signalling chain.

In the aforementioned escape mechanism, platelets docking in the provision of growth factors play a role, as can be illustrated the following steps:
1 A platelet docks to the platelet receptor on the membrane of a growth committed cell and thereupon is activated. In the course of this process, the contents of its alpha-granules are released.
2 These contain among other substances also growth factors, which now are available to dock to Receptor Tyrosine Kinases (RTK)
3 Thereupon the RTK activate Ras in the canonical Ras-Raf-MEK-ERK pathway (left). This pathway is a main signaling cascade in cell proliferation, reaching as an activation cascade MEK, which function it is to phosphorylate and activate ERK. Therapeutic approaches to treat cancer interfere with the pathway by providing MEK inhibitors blocking the phosphorylation of ERK and thereby stopping further signalling towards cell proliferation. MEK inhibitors have proven as a promising anti-cancer agent promoting apoptosis of tumour cells and preventing their cell proliferation.
4 However, in the clinical situation often the development of resistance to MEK inhibitors is observed. In particular, unphosphorylated ERK can upregulate and/or activate the MAP3K1 phosphokinase.
5 The MAP3K1 phosphokinase dependent pathway (left) can among other functions also induce nuclear synthesis of m-RNA for other Receptor Tyrosine Kinases, such as e.g. ERBB3.
6 Through the activation of the MAP3K1 phosphokinase synthesis of mRNA (such as ERBB3) is promoted.
7 ERBB3 and similar Receptor Tyrosine Kinases may upon reaction with growth factors released from activated platelet start as an alternative route a MAP3K1 dependent pathway to promote cell proliferation. By bypassing the Ras-Raf-MEK-ERK pathway, the cell has thus developed a resistance against the MEK inhibitor and can continue proliferation.

As described herein, negatively charged glycosaminoglycans may inhibit the adherence of platelets to platelet receptors expressed on the cell surface of growth committed cells, thus also inhibiting the escape route via an activation of MAP3K1. Thereby a resistance towards the MEK inhibitor may be abolished.

FIG. 2 illustrates the effect of a combination of a MEK-inhibitor treatment together with the administration of a negatively charged glycosaminoglycan.

A negatively charged glycosaminoglycan prevents the platelet from docking to the cell and thus the provision of growth factors. Due to the absence of available growth factors, the alternative signalling route via MAP3K1 cannot be activated and the development of a resistance towards a MEK inhibitory treatment is impeded.

The MEK inhibitor thus retains its anticancer and antiproliferative effectivity due a combined administration of the negatively charged glycosaminoglycan, which acts upstream of the RTK's in the chain of biological processes leading to tumour growth.

Such a combined treatment is particularly useful in the treatment of metastases. 90 percent of patients dying of cancer do so because of metastases. These are daughter tumours, typically arising in other tissues than the primary tumour tissue. At the onset of a metastases, when the tumour is at a single cell stage, either circulating in the blood or dwelling in a metastatic niche or if the tumour is still smaller than some millimetres in diameter, the combined treatment of a negatively charged glycosaminoglycan and a MEK inhibitor is particularly efficient. The treatment therefore also presents new opportunities to selectively prevent metastases.

EXAMPLES

The invention is further described by the following examples. These are not intended to limit the scope of the invention.

Example 1

The experiment is performed on cancerous cells that have developed a resistance against the MEK inhibitor Selumetinib. As described in Little et al. 2011 in detail cancerous cells that have developed a resistance against the MEK inhibitor Selumetinib are generated by growing colorectal cancer cell lines harboring mutations in BRAF (COL0205 and HT29 lines) or KRAS (HCT116 and LoVo lines) in the presence of increasing concentrations of AZD6244 (Selumetinib) without clonal selection until they grow apparently normally in 1 µm, 2 µM or 4 µM of the drug.

For each of the cancerous cells lines that have developed a resistance against the MEK inhibitor Selumetinib the following steps are performed:

Three populations of cells are cultivated in the presence of the inhibitor under serum-free conditions.

For a first population of the cells PPS is added to the cell culture dishes, while for a second population, i.e. the control cells, no PPS is added.

For a third population of the cells DXS is added to the cell culture dishes.

Each day all cell populations are co-incubated with platelets for 30 minutes, which are subsequently washed away.

Control cells in the growth cycle express platelet receptors on their surface. Platelets adhere to the control cells and release growth factors from their alpha granules. The control cells will take up the factors and proceed through the cell cycle, even in the presence of the MEK inhibitor.

For the first and third population of cells, the PPS and DXS prevents the platelet from adhering to the cancerous cells, therefore no platelet-derived growth factors are released and proliferation is impeded.

While control cancerous cells continue to grow and divide, even in the presence of a MEK inhibitor, the cell populations which are incubated in the presence of the MEK inhibitor and PPS or DXS perish.

Example 2

The second experiment is performed as described for Example 1 except that cells are cultivated in the presence of the MEK inhibitor CI-1040 (PD184352).

As described in Little et al. 2011 in detail cancerous cells that have developed a resistance against the MEK inhibitor PD184352 are generated by growing colorectal cancer cell lines harboring mutations in BRAF (COL0205) or KRAS (HCT116) in the presence of increasing concentrations of AZD6244 (Selumetinib) without clonal selection until they grow apparently normally in 1 µm, 2 µM or 4 of the drug.

For each of the cancerous cells lines that have developed a resistance against the MEK inhibitor CI-1040 (PD184352) the cultivation steps as in Example 1 are performed, except that the cells are cultivated in the presence of the MEK inhibitor CI-1040 (PD184352).

While control cancerous cells continue to grow and divide, even in the presence of the MEK inhibitor CI-1040 (PD184352), the cell populations which are incubated in the presence of the MEK inhibitor CI-1040 (PD184352) and the PPS or DXS perish.

Example 3

The third experiment is performed as described for Example 1 except that cells that have developed a resistance against the MEK inhibitor trametinib (GSK1120212) are used and cultivated in the presence of the MEK inhibitor trametinib.

As described in Vujic et al. 2014 in detail cancerous cells that have developed a resistance against the MEK inhibitor trametinib are generated by growing Human NRAS mutant melanoma cell lines DO4 and MM415 in the presence of increased concentrations of trametinib (GSK1120212) over a period of approximately 6 months.

For each of the cancerous cell lines that have developed a resistance against the MEK inhibitor trametinib the cultivation steps as in Example 1 are performed, except that the cells are cultivated in the presence of the MEK inhibitor trametinib.

While control cancerous cells continue to grow and divide, even in the presence of the the MEK inhibitor trametinib, the cell populations which are incubated in the presence of the MEK inhibitor trametinib and the PPS or DXS perish.

Example 4

The fourth experiment is performed as described for Example 1 except that cells that have developed a resistance against the Raf inhibitor vemurafenib are used and cultivated in the presence of the Raf inhibitor vemurafenib.

As described in Sandri et al. 2016 in detail cancerous cells that have developed a resistance against the Raf inhibitor vemurafenib are generated by growing melanoma cell line SK-MEL-28 carrying the $BRAF^{V600E}$ mutation in the presence of 0.5-0.6 µM vemurafenib for 4-6 weeks and subsequently isolating clonal colonies.

For each of the cancerous cells lines that have developed a resistance against the Raf inhibitor vemurafenib the cultivation steps as in Example 1 are performed, except that the cells are cultivated in the presence of the Raf inhibitor vemurafenib.

While control cancerous cells continue to grow and divide, even in the presence of the the Raf inhibitor vemurafenib, the cell populations which are incubated in the presence of the Raf inhibitor vemurafenib and the PPS or DXS perish.

Example 5

The fifth experiment is performed as described for Example 1 except that cells that have developed a resistance against the Raf inhibitor sorafenib are used and cultivated in the presence of the Raf inhibitor sorafenib.

As described in Chen et al. 2011 in detail cancerous cells that have developed a resistance against the Raf inhibitor sorafenib are generated by growing the human Hepatocellular carcinoma (HCC) Huh7 in a long term exposure to sorafenib.

For each of the cancerous cells lines that have developed a resistance against the Raf inhibitor sorafenib the cultivation steps as in Example 1 are performed, except that the cells are cultivated in the presence of the Raf inhibitor sorafenib.

While control cancerous cells continue to grow and divide, even in the presence of the the Raf inhibitor sorafenib, the cell populations which are incubated in the presence of the Raf inhibitor sorafenib and the PPS or DXS perish.

Example 6

The sixth experiment is performed as described for Example 1 except that cells that have developed a resistance against the Raf inhibitor dabrafenib are used and cultivated in the presence of the Raf inhibitor dabrafenib.

As described in Caparorali et al. 2011 in detail cancerous cells that have developed a resistance against the Raf inhibitor dabrafenib are generated by growing the human melanoma cell line A375 in gradually increasing concentrations of dabrafenib (from 1 nM up to 1.5 µM) over a period of 4 months and subsequently maintaining the dabrafenib-resistance cell lines in CM supplemented with 1.5 µM dabrafenib.

For each of the cancerous cells lines that have developed a resistance against the Raf inhibitor dabrafenib the cultivation steps as in Example 1 are performed, except that the cells are cultivated in the presence of the Raf inhibitor dabrafenib.

While control cancerous cells continue to grow and divide, even in the presence of the the Raf inhibitor dabrafenib, the cell populations which are incubated in the presence of the Raf inhibitor dabrafenib and the PPS or DXS perish.

Example 7

The seventh experiment is performed as described for Example 1, except that the cancerous cells are resistant against an RTK inhibitor and the three populations of cells are cultivated in the presence of the RTK inhibitor.

While control cancerous cells continue to grow and divide, even in the presence of the RTK inhibitor, the cell populations incubated in the additional presence of PPS or DXS perish.

REFERENCES

Anderson N G., Mailer J. L., Tonks N. K., Sturgill T. W., Requirement for integration of signals from two distinct phosphorylation pathways for activation of MAP kinase, *Nature,* 343:651-653 (1990).

Caporali et al. Targeting the PI3K/AKT/mTOR pathway overcomes the stimulating effect of dabrafenib on the invasive behavior of melanoma cells with acquired resistance to the BRAF inhibitor, *International Journal of Oncology* 49: 1164-1174 (2016).

Chapman, P. B. et al. Improved survival with vemurafenib in melanoma with BRAF V600E mutation. *N. Engl. J. Med.* 364:2507-2516 (2011).

Chen et al. Activation of Phosphatidylinositol 3-Kinase/Akt Signaling Pathway Mediates Acquired Resistance to Sorafenib in Hepatocellular Carcinoma Cells, *The Journal of Pharmacology and Experimental Therapeutics,* 337:155-161.

Cole et al. Synthetic Heparan Sulfate Oligosaccharides Inhibit Endothelial Cell Functions Essential for Angiogenesis, *PLoS One,* 5(7):e11644

Dooley A. J. et al. Intermittent dosing with vemurafenib in BRAF V600E-mutant melanoma: Review of case series, *Therapeutic Advances in Medical Oncology,* 6(6): 262-266 (2014).

Eroglu Z., Ribas A., Combination therapy with BRAF and MEK inhibitors for melanoma: latest evidence and place in therapy, Therapeutic Advances in Medical Oncology, 8(1): 48-56 (2016).

Flaherty, K. T. et al. Inhibition of mutated, activated BRAF in metastatic melanoma. *N. Engl. J. Med.* 363:809-819 (2010).

Grimaldi M. et al., Combined BRAF and MEK Inhibition with Vemurafenib and Cobimetinib for Patients with Advanced Melanoma, *European Oncology & Haematology,* 13:1-5 (2017).

Harter K., Levine M., Henderson O., Anticoagulation Drug Therapy: A Review, *Western Journal of Emergency Medicine.* 16:1 (2015).

Hauschild, A. et al. Dabrafenib in BRAF-mutated metastatic melanoma: a multicentre, open-label, phase 3 randomised controlled trial. *Lancet* 380:358-365 (2012).

Holderfield M., Deuker M. M., McCormick F., McMahon M., Targeting RAF kinases for cancer therapy: BRAF mutated melanoma and beyond, *Nat Rev Cancer,* 14:455-467 (2014).

Hoshino R., Chatani Y., Yamori T., Tsuruo T., Oka H., Yoshida O., Shimada Y., Ari-i S., Wada H., Fujimoto J., Kohno M., Constitutive activation of the 41-/43-kDa mitogen-activated protein kinase signalling pathway in human tumours, *Oncogene,* 18:813-822 (1999).

Little et al. *Amplification of Driving Oncogene, KRAS or BRAF, underpins resistance acquired to MEK1/2 inhibitors in colorectal cancer cells,* Science Signalling 4 (166) ra17 (2011).

Lugowska I., Kosela-Paterczyk H., Kozak K., Rutkowski P., Trametinib: a MeK inhibitor for management of metastatic melanoma, *OncoTargets and Therapy,* 8:2251-2259 (2015).

McCubrey J. A, Steelman L. S., Chappell W. H., Abrams S. L., Wong E. W. T., Chang F., Lehmann B., David M. T., Milella M., Tafuri A., Stivala F., Libra M., Evangelisti J. B. C., Martelli A. M., Franklin R. A., Roles of the Raf/MEK/ERK pathway in cell growth, malignant transformation and drug resistance, *Biochimica et Biophysica Acta (BBA)—Molecular Cell Research,* 1773:1263-1284 (2007).

Milhavet O., Gary D. S., Mattson M. P., RNA interference in biology and medicine, *Pharmacol Rev.,* 55:629-48 (2003).

Modery-Pawlowski, C. L., Master, A. M., Pan, V., Howard, G., & Gupta, A. S., A Platelet-Mimetic Paradigm for Metastasis-Targeted Nanomedicine Platforms. *Biomacromolecules,* 14(3):910-919 (2013).

Opalinska J. B., Gewirtz A. M., Therapeutic potential of antisense nucleic acid molecules, *Sci STKE,* 206:pe47 (2003).

Peyssonnaux C., Eychène A., The Raf/MEK/ERK pathway: new concepts of activation, *Biology of the Cell,* 93: 53-62 (2001).

Poulikakos P. I. et al., Resistance to MEK Inhibitors: Should We Co-Target Upstream?, *Science Signalling* 4(166): pe16 (2011).

Rhomberg A. J., Ernst S., Sasisekharan R., and Biemann K., Mass spectrometric and capillary electrophoretic investigation of the enzymatic degradation of heparin-like glycosaminoglycans, *Proc. Natl. Acad. Sci.,* 95:4176-4181 (1998).

Rosen N. et al. Tumour adaptation and resistance to RAF inhibitors, *Nature Medicine,* 19:11 (2013)

Sandri S. et al. Vemurafenib resistance increases melanoma invasiveness and modulates the tumor microenvironment by MMP-2 upregulation, *Pharmacological Research* 111: 523-533 (2016).

Schwartz, C. F., Kilgore, K. S., Homeister, J. W., Levy, B. A., Lucchesi, B. R., & Bolling, S. F., Increased rat cardiac allograft survival by the glycosaminoglycan pentosan polysulfate. *Journal of Surgical Research,* 86: 24-28 (1999).

Sivaraman, V. S., Wang, H., Nuovo, G. J., & Malbon, C. C. Hyperexpression of mitogen-activated protein kinase in human breast cancer. *Journal of Clinical Investigation,* 99:1478-1483 (1997).

Takagi, S., Sato, S., Oh-hara, T., Takami, M., Koike, S., Mishima, Y., Hatake K., Fujita, N., Platelets Promote Tumour Growth and Metastasis via Direct Interaction between Aggrus/Podoplanin and CLEC-2. *PLoS ONE,* 8(8):e73609 (2013).

Turnbull J. E., Hopwood J. J., Gallagher J. T., Strategy for rapid sequencing of heparan sulfate and heparin saccharides, *Proc. Natl. Acad. Sci.,* 96:2698-2703 (1999).

Vujic et al. Metformin and trametinib have synergistic effects on cell viability and tumor growth in NRAS mutant cancer, *Oncotarget* (November 2014).

Wang, Z., Zhang, F., Dordick, J. S., & Linhardt, R. J. Molecular Mass Characterization of Glycosaminoglycans with Different Degrees of Sulfation in Bioengineered Heparin Process by Size Exclusion Chromatography. *Current Analytical Chemistry*, 8(4), 506-511 (2012).

Zhao, Y., Adjei, A. A., The clinical development of MEK inhibitors. *Nat. Rev. Clin. Oncol.* 11:385-400 (2014).

What is claimed is:

1. A method of treatment of cancer in a subject comprising:
   administering to the subject a combined administration of:
   (1) a negatively charged glycosaminoglycan, wherein said negatively charged glycosaminoglycan is sulfated and characterised by the absence of the terminal pentasaccharide of Heparin, and
   (2) an inhibitor of the MAPK/ERK pathway, wherein the cancer comprises cancerous cells that are resistant to, or are at elevated risk of developing resistance to an inhibitor of the MAPK/ERK pathway, or a combination thereof.

2. The method according to claim 1, wherein the degree of sulfation of said negatively charged glycosaminoglycan is >1.0.

3. The method according to claim 1, wherein said negatively charged glycosaminoglycan is characterised by the absence of a pentasaccharide GlcNAc/NS(6S)-GlcA-GlcNS(3S,6S)-IdoA(2S)-GlcNS(6S).

4. The method according to claim 1, wherein said negatively charged glycosaminoglycan exhibits an average molecular weight of about 5000 to about 12000 daltons.

5. The method according to claim 1, wherein the inhibitor of the MAPK/ERK pathway for the combined administration is a MEK Inhibitor.

6. The method according to claim 5, wherein the MEK inhibitor is Selumetinib.

7. The method according to claim 1, wherein the MEK inhibitor is selected from the group consisting of Trametinib (GSK1120212), Cobimetinib or XL518, Binimetinib (MEK162), PD-325901, CI-1040, PD035901, and TAK-733.

8. The method according to claim 1, wherein the inhibitor of the MAPK/ERK pathway for combined administration is a Raf Inhibitor.

9. The method according to claim 1, wherein the cancer comprises cancerous cells that exhibit the presence of one or more ErbB-family proteins on the cell surface.

10. The method according to claim 1, wherein the cancer comprises cancerous cells that exhibit increased expression (up-regulation) of at least one of one or more ErbB-family proteins or increased ErbB signalling compared to an appropriate (non-cancerous) control cell.

11. The method according to claim 10, wherein the up-regulated ErbB-family protein is Her1 (EGFR, ErbB1), Her2 (Neu, ErbB2), Her3 (ErbB3), or Her4 (ErbB4).

12. The method according to claim 1 further comprising:
   allowing sufficient time for the combined administration that forms a composition to treat the cancer, the cancer being one of: leukaemia, lymphoma, melanoma, non-small cell lung cancer, glioma, hepatocellular (liver) carcinoma, glioblastoma, carcinoma of the thyroid, bile duct, bone, gastric, brain/CNS, head and neck, hepatic, stomach, prostate, breast, renal, testicular, ovarian, skin, cervical, lung, muscle, neuronal, oesophageal, bladder, lung, uterine, vulval, endometrial, kidney, colorectal, pancreatic, pleural/peritoneal membranes, salivary gland, and epidermoid tumours and haematological malignancies, and metastases of any of the aforementioned.

13. The method of claim 1 wherein the cancer is a tumour associated with the MAPK/ERK (Ras-Raf-MEK-ERK) pathway or which is dependent alone, or in part, on the biological activity of the MAPK/ERK (Ras-Raf-MEK-ERK) pathway.

14. The method of claim 1 wherein the administration is local administration of said negatively charged glycosaminoglycan in proximity to a tumour of the cancer.

15. The method of claim 14 wherein the local administration is by injection, transmucosaL or transdermal.

16. The method of claim 1 wherein the administration is sequential of the negatively charged glycosaminoglycan and the inhibitor of the MAPK/ERK pathway, or vice versa.

17. A method of treatment of cancer, comprising the combined administration of
   (1) a negatively charged sulfated polysaccharide, wherein said sulfated polysaccharide is characterised by the absence of the terminal pentasaccharide of Heparin, and
   (2) an inhibitor of the MAPK/ERK pathway, and
   wherein the cancer comprises cancerous cells that are resistant to, or are at elevated risk of developing resistance to an inhibitor of the MAPK/ERK pathway, or a combination thereof.

18. The method according to claim 17, wherein the negatively charged sulfated polysaccharide is pentosan polysulfate (PPS).

19. The method according to claim 17, wherein the negatively charged sulfated polysaccharide is dextran sulfate (DXS).

20. The method according to claim 17, wherein the cancer comprises cancerous cells that exhibit the presence of one or more ErbB-family proteins on the cell surface.

* * * * *